United States Patent
Foad et al.

(10) Patent No.: US 12,178,398 B2
(45) Date of Patent: *Dec. 31, 2024

(54) ELECTRONIC ASSEMBLIES INCLUDING A CONFORMAL MOISTURE BARRIER

(71) Applicant: Intuitive Surgical Operations, Inc., Sunnyvale, CA (US)

(72) Inventors: Majeed A. Foad, Sunnyvale, CA (US); John A Barton, San Jose, CA (US); Jonathan D. Halderman, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/203,418

(22) Filed: May 30, 2023

(65) Prior Publication Data

US 2023/0320572 A1    Oct. 12, 2023

Related U.S. Application Data

(63) Continuation of application No. 17/012,836, filed on Sep. 4, 2020, now Pat. No. 11,700,993.

(60) Provisional application No. 62/896,764, filed on Sep. 6, 2019.

(51) Int. Cl.
*A61B 1/00* (2006.01)
*A61B 1/04* (2006.01)
*H05K 3/28* (2006.01)
*A61L 2/18* (2006.01)
*C23C 16/455* (2006.01)

(52) U.S. Cl.
CPC ...... *A61B 1/00137* (2013.01); *A61B 1/00142* (2013.01); *A61B 1/04* (2013.01); *H05K 3/282* (2013.01); *H05K 3/284* (2013.01); *A61L 2/18* (2013.01); *C23C 16/45555* (2013.01)

(58) Field of Classification Search
CPC ... A61B 1/00137; A61B 1/00142; A61B 1/04; A61B 1/051; H05K 3/282; H05K 3/284; H05K 2203/095; H05K 2203/1322; A61L 2/18; C23C 16/45555; C23C 16/0245
See application file for complete search history.

(56) References Cited

U.S. PATENT DOCUMENTS

| | | | |
|---|---|---|---|
| 11,700,993 B2 * | 7/2023 | Foad | A61B 1/04 600/476 |
| 2014/0151656 A1 * | 6/2014 | Zeng | C23C 16/45525 428/411.1 |
| 2017/0159178 A1 * | 6/2017 | Baker | C23C 28/42 |
| 2018/0237909 A1 | 8/2018 | Yun et al. | |

(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Bao Q Truong

(57) ABSTRACT

A method includes forming, by atomic layer deposition, a first barrier layer on a surface of a printed circuit board ("PCB") and on an outer surface of an electrical component attached to the surface of the PCB; forming an adhesion promotion layer on a surface of the first barrier layer; and forming, on the adhesion promotion layer, a second barrier layer including Parylene.

20 Claims, 11 Drawing Sheets

(56) References Cited

U.S. PATENT DOCUMENTS

2020/0365534 A1* 11/2020 Darmawikarta .... H01L 21/4846
2021/0068631 A1 3/2021 Foad et al.

* cited by examiner

ELECTRONIC ASSEMBLIES INCLUDING A CONFORMAL MOISTURE BARRIER

RELATED APPLICATIONS

The present application is a continuation application of U.S. patent application Ser. No. 17/012,836, filed Sep. 4, 2020, which claims priority to U.S. Provisional Patent Application No. 62/896,764, filed on Sep. 6, 2019, the contents of which are hereby incorporated by reference in their entirety.

BACKGROUND INFORMATION

After surgical instruments are used in a surgical procedure, the surgical instruments must be sterilized before they can be used in another surgical procedure. The sterilization process may include, for example, subjecting the surgical instruments to a chemical bath, ultrasonic agitation, and/or high autoclave temperatures. However, the harsh conditions of the sterilization process may, over time, degrade electrical components included in some surgical instruments, such as endoscopes, and thereby affect the performance and operation of such surgical instruments and shorten the useful life of such surgical instruments.

SUMMARY

The following description presents a simplified summary of one or more aspects of the methods and systems described herein in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects of the methods and systems described herein in a simplified form as a prelude to the more detailed description that is presented below.

An exemplary electronic assembly may comprise a printed circuit board ("PCB"); an electrical component attached to a surface of the PCB; and a conformal barrier disposed on at least a portion of the surface of the PCB and on an outer surface of the electrical component, the conformal barrier comprising a first barrier layer comprising an atomic layer deposited ("ALD") film, and a second barrier layer comprising Parylene.

An exemplary method may comprise forming, by atomic layer deposition, a first barrier layer on at least a portion of a surface of a PCB and on an outer surface of an electrical component attached to the surface of the PCB, and forming, on the first barrier layer, a second barrier layer comprising Parylene.

An exemplary imaging device may comprise a camera head and a shaft that extends from the camera head and that comprises a distal end configured to be positioned within a surgical area of a patient, and one or more channels within the shaft that are configured to provide signals to the camera head, wherein the camera head houses a PCB and an electrical circuit on the PCB, the electrical circuit configured to receive the signals and generate data based on the signals, and a conformal barrier is disposed on at least a portion of the PCB and on the electrical circuit, the conformal barrier comprising an ALD film.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements. Furthermore, the figures are not necessarily drawn to scale as one or more elements and layers shown in the figures may be enlarged to facilitate recognition.

DETAILED DESCRIPTION

Figure 1:
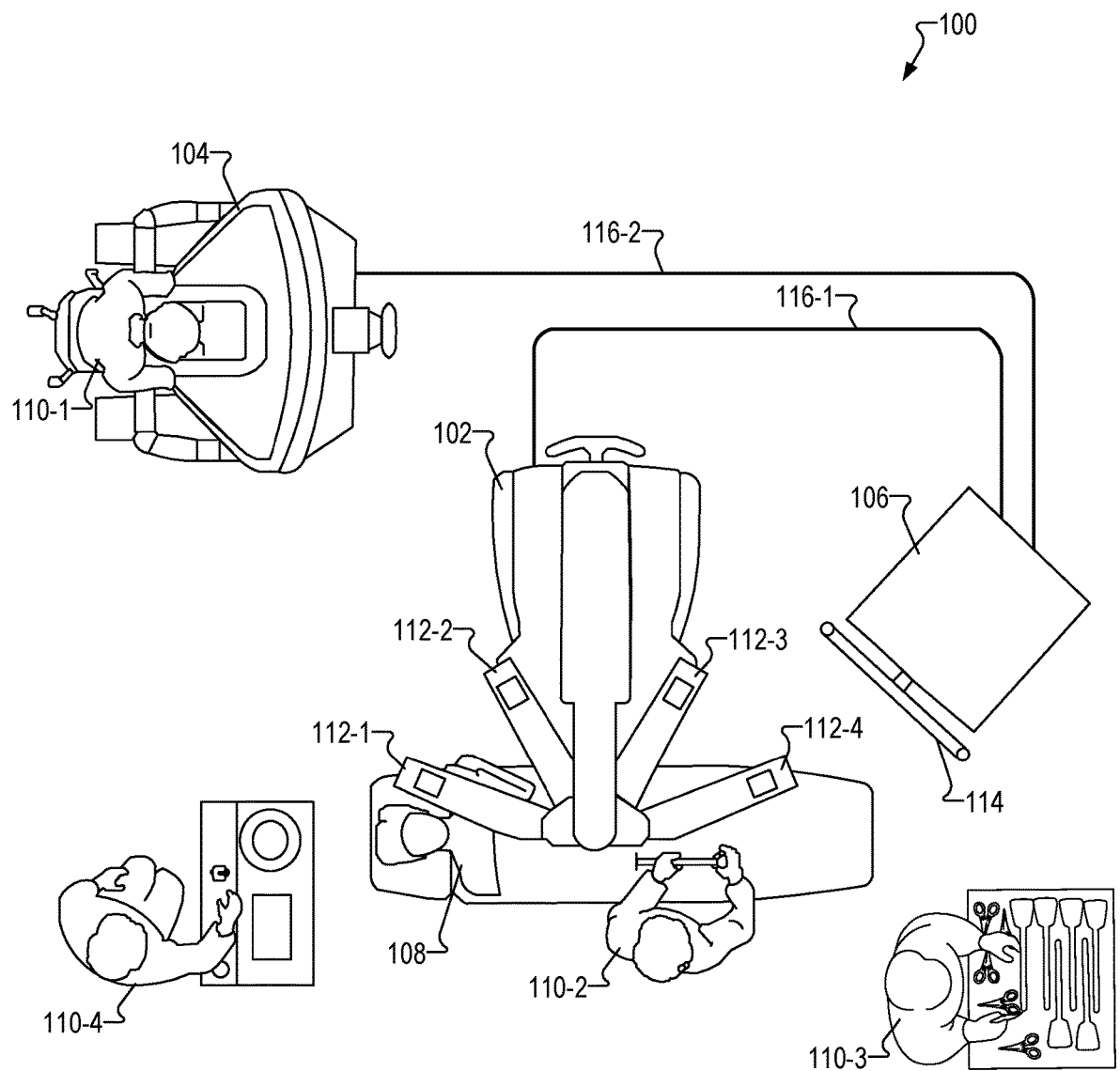
FIG. 1 illustrates an exemplary computer-assisted surgical system according to principles described herein.

Electronic assemblies and methods of forming electronic assemblies are described herein. As will be described below in more detail, an electronic assembly may include a PCB, an electrical component attached to a surface of the PCB, and a conformal barrier disposed on at least a portion of the surface of the PCB and on an outer surface of the electrical component. The conformal barrier may include a first barrier layer comprising an ALD film and a second barrier layer comprising Parylene.

In some examples the PCB may be included in a surgical instrument configured to be used in a surgical procedure (e.g., a minimally invasive surgical procedure performed by a robotic surgical system). To illustrate, the PCB may be housed within a camera head of an imaging device (e.g., an endoscope). A shaft that includes one or more channels therein may extend from the camera head. A distal end of the shaft may include one or more image sensors configured to receive light (e.g., light reflecting from internal patient anatomy) when positioned within a surgical area associated with a patient and generate data representative of images of the surgical area. The image sensors may transmit the data to the camera head by way of the one or more channels within the shaft. Electrical circuitry on the PCB may be configured to process the data and/or transmit the data to a computing device located off the PCB by way of an electrical cable. For example, the electrical circuitry may transmit the data by way of the electrical cable to a computing device that is a part of a display system. The display system may use the data to display the one or more images.

Various benefits may be provided by the electronic assemblies described herein. For example, the conformal barrier of the electronic assemblies described herein includes an atomic layer deposited ("ALD") film, which provides an ultra-high moisture barrier to protect a PCB and/or any electrical components attached thereto from moisture that is present during a surgical procedure and during a sterilization process. Additionally, the ALD film is not easily degraded over time by sterilization processing because the ALD film is stable at temperatures common to sterilization processing (e.g., up to about 150° C.), is physically hard, and is chemically inert. As a result, reliable operation of the PCB and electrical components attached thereto may be prolonged, which may prolong the useful life of the surgical instrument in which the PCB is included. In some examples a conformal barrier may also include another barrier layer, such as a Parylene film, which provides an additional moisture barrier and additional protection from sterilization processing and handling. These and other benefits of the electronic assemblies described herein will be made apparent in the description that follows.

Various embodiments will now be described in more detail with reference to the figures. The systems and methods described herein may provide one or more of the benefits mentioned above and/or various additional and/or alternative benefits that will be made apparent herein.

The electronic assemblies described herein may be implemented as part of or in conjunction with a computer-assisted surgical system. As such, an exemplary computer-assisted surgical system will now be described. The following exemplary computer-assisted surgical system is illustrative and not limiting, as the systems and apparatuses described herein may be implemented as part of or in conjunction with other suitable surgical systems.

FIG. 1 illustrates an exemplary computer-assisted surgical system 100 ("surgical system 100"). As shown, surgical system 100 may include a manipulating system 102, a user control system 104, and an auxiliary system 106 communicatively coupled one to another.

Surgical system 100 may be utilized by a surgical team to perform a computer-assisted surgical procedure on a patient 108. As shown, the surgical team may include a surgeon 110-1, an assistant 110-2, a nurse 110-3, and an anesthesiologist 110-4, all of whom may be collectively referred to as "surgical team members 110." Additional or alternative surgical team members may be present during a surgical session as may serve a particular implementation.

While FIG. 1 illustrates an ongoing minimally invasive surgical procedure, surgical system 100 may similarly be used to perform open surgical procedures or other types of surgical procedures that may similarly benefit from the accuracy and convenience of surgical system 100. Additionally, it will be understood that the surgical session throughout which surgical system 100 may be employed may not only include an operative phase of a surgical procedure, as is illustrated in FIG. 1, but may also include preoperative, postoperative, and/or other suitable phases of the surgical procedure. A surgical procedure may include any procedure in which manual and/or instrumental techniques are used on a patient to investigate, diagnose, or treat a physical condition of the patient. Additionally, a surgical procedure may include any procedure that is not performed on a live patient, such as a calibration procedure, a training procedure, and an experimental or research procedure.

As shown in FIG. 1, manipulating system 102 may include a plurality of manipulator arms 112 (e.g., manipulator arms 112-1 through 112-4) to which a plurality of surgical instruments (not shown) may be coupled. Each surgical instrument may be implemented by any suitable surgical tool (e.g., a tool having tissue-interaction functions), medical tool, monitoring instrument (e.g., an endoscope), sensing instrument (e.g., a force-sensing surgical instrument), diagnostic instrument, or the like that may be used for a computer-assisted surgical procedure (e.g., by being at least partially inserted into patient 108 and manipulated to perform a computer-assisted surgical procedure on patient 108). Some surgical instruments may include one or more PCBs for supporting electrical circuitry, such as circuitry used in the robotic and/or teleoperation control of the surgical instrument. While manipulating system 102 is depicted and described herein as including four manipulator arms 112, it will be recognized that manipulating system 102 may include only a single manipulator arm 112 or any other number of manipulator arms as may serve a particular implementation.

Manipulator arms 112 and/or surgical instruments attached to manipulator arms 112 may include one or more displacement transducers, orientational sensors, and/or positional sensors used to generate raw (i.e., uncorrected) kinematics information (hereinafter "surgical system sensors"). One or more components of surgical system 100 may be configured to use the kinematics information to track (e.g., determine positions of) and/or control the surgical instruments.

Surgical instruments attached to manipulator arms 112 may each be positioned at a surgical area associated with a patient. A "surgical area" may, in certain examples, be entirely disposed within a patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments being used to perform the surgical procedure are located. In other examples, a surgical area may be at least partially disposed external to the patient at or near where a surgical procedure is planned to be performed, is being performed, or has been performed on the patient. For instance, surgical system 100 may be used to perform an open surgical procedure such that part of the surgical area (e.g., tissue being operated on) is internal to the patient while another part of the surgical area (e.g., a space around the tissue where one or more surgical instruments may be disposed) is external to the patient. A surgical instrument may be referred to as being positioned or located at or within a surgical area when at least a portion of the surgical instrument (e.g., a distal portion of the surgical instrument) is located within the surgical area.

User control system 104 may be configured to facilitate control by surgeon 110-1 of manipulator arms 112 and surgical instruments attached to manipulator arms 112. For example, surgeon 110-1 may interact with user control system 104 to remotely move or manipulate manipulator arms 112 and the surgical instruments. To this end, user control system 104 may provide surgeon 110-1 with images (e.g., high-definition 3D images) of a surgical area associated with patient 108 as captured by an imaging device (e.g., an endoscope). In certain examples, user control system 104 may include a stereo viewer having two displays where stereoscopic images of a surgical area associated with patient 108 and generated by a stereoscopic imaging system may be viewed by surgeon 110-1. Surgeon 110-1 may utilize the imagery to perform one or more procedures with one or more surgical instruments attached to manipulator arms 112.

To facilitate control of surgical instruments, user control system 104 may include a set of master controls (not shown). These master controls may be manipulated by surgeon 110-1 to control movement of surgical instruments (e.g., by utilizing robotic and/or teleoperation technology). The master controls may be configured to detect a wide variety of hand, wrist, and finger movements by surgeon 110-1. Based on the user manipulation of the master controls, control signals may be generated and transmitted to manipulator arms 112 and/or surgical instruments attached to manipulator arms 112 to control movement or operation of the manipulator arms 112 and/or surgical instruments. In this manner, surgeon 110-1 may intuitively perform a surgical procedure using one or more surgical instruments.

User control system 104 may further be configured to facilitate control by surgeon 110-1 of other components of surgical system 100. For example, surgeon 110-1 may interact with user control system 104 to change a configuration or operating mode of surgical system 100, to change a display mode of surgical system 100, to generate additional control signals used to control surgical instruments attached to manipulator arms 112, to facilitate switching control from one surgical instrument to another, or to perform any other suitable operation. To this end, user control system 104 may also include one or more input devices (e.g., foot pedals, buttons, switches, etc.) configured to receive input from surgeon 110-1.

Auxiliary system 106 may include one or more computing devices configured to perform primary processing operations of surgical system 100. The one or more computing devices included in auxiliary system 106 may control and/or coordinate operations performed by various other components (e.g., manipulating system 102, surgical instruments attached to manipulator arms 112, and/or user control system 104) of surgical system 100. For example, a surgical instrument controller may receive and/or generate control signals and transmit the control signals to manipulating system 102 (e.g., to electrical circuitry attached to a PCB included in a surgical instrument attached to a manipulator arm 112). As another example, auxiliary system 106 (e.g., the surgical instrument controller) may receive and process image data representative of images captured by an imaging device (e.g., an endoscope) attached to a manipulator arm 112 and transmit the image data to user control system 104 for display on a display device (e.g., a stereo viewer) included in user control system 104.

In some examples, auxiliary system 106 may be configured to present visual content to surgical team members 110 who may not have access to the images provided to surgeon 110-1 at user control system 104. To this end, auxiliary system 106 may include a display monitor 114 configured to display one or more user interfaces, such as images (e.g., 2D images) of the surgical area, information associated with patient 108 and/or the surgical procedure, and/or any other visual content as may serve a particular implementation. For example, display monitor 114 may display images of the surgical area together with additional content (e.g., graphical content, contextual information, etc.) concurrently displayed with the images. In some embodiments, display monitor 114 is implemented by a touchscreen display with which surgical team members 110 may interact (e.g., by way of touch gestures) to provide user input to surgical system 100.

In some examples, auxiliary system 106 (e.g., a surgical instrument controller) may include one or more power sources configured to provide electrical power to surgical instruments attached to manipulator arms 112. In additional examples, auxiliary system 106 (e.g., the surgical instrument controller) may include one or more illumination sources configured to emit light and convey the emitted light to a surgical instrument (e.g., an endoscope) attached to a manipulator arm.

Manipulating system 102, user control system 104, and auxiliary system 106 may be communicatively coupled one to another in any suitable manner. For example, as shown in FIG. 1, manipulating system 102 and auxiliary system 106 may be communicatively coupled by way of connection 116-1, and auxiliary system 106 and user control system 104 may be communicatively coupled by way of connection 116-2. Connection 116-1 may represent, for example, one or more cables connected to manipulating system 102 and/or surgical instruments attached to manipulator arms 112. Such cables may include, for example, one or more wired communication lines, power lines, optical fibers, and/or light guides. Connection 116-2 may represent any wired or wireless communication link as may serve a particular implementation. Manipulating system 102, user control system 104, and auxiliary system 106 may each include one or more wired or wireless communication interfaces, such as one or more connection systems, local area network interfaces, Wi-Fi network interfaces, cellular interfaces, etc.

In some examples the electronic assemblies described herein may be included in or part of a surgical instrument, such as an imaging device (e.g., a stereoscopic endoscope). Accordingly, an exemplary imaging device and imaging system will now be described. The following exemplary imaging device and imaging system are illustrative and not limiting, as the electronic assemblies described herein may be implemented as part of or in conjunction with other suitable surgical instruments (e.g., a cautery instrument, a needle driver, a scissors-type instrument, a stapler, etc.).

Figure 2:
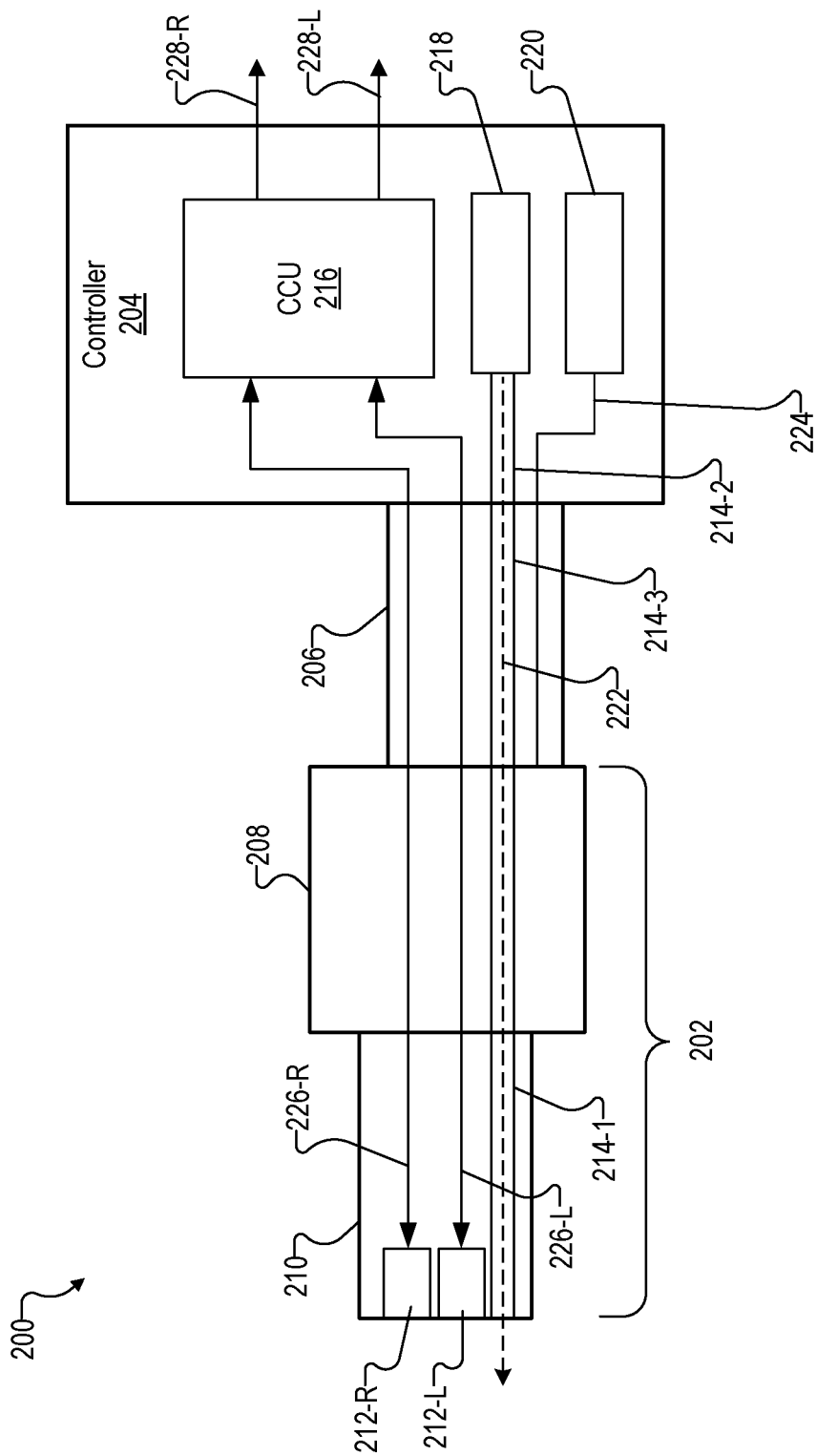
FIG. 2 illustrates an exemplary imaging system according to principles described herein.

FIG. 2 illustrates a functional diagram of an exemplary imaging system 200 that may be used to capture images of a scene (e.g., a surgical area associated with patient 108). As shown, imaging system 200 includes an imaging device 202, a controller 204, and a cable 206 that interconnects imaging device 202 and controller 204. Imaging system 200 may include additional or alternative components as may serve a particular implementation. For example, imaging system 200 may include various optical and/or electrical signal transmission components (e.g., wires, lenses, optical fibers, choke circuits, waveguides, etc.).

Imaging device 202 may be implemented by an endoscope or other camera device configured to capture images of a scene. As shown, imaging device 202 includes a camera head 208, a shaft 210 coupled to and extending away from camera head 208, image sensors 212 (e.g., a right-side image sensor 212-R and a left-side image sensor 212-L) at a distal end of shaft 210, and a first illumination channel 214-1. In the example of FIG. 2, imaging device 202 is stereoscopic. In other examples imaging device 202 may be monoscopic (e.g., by including one image sensor 212 instead of two image sensors 212).

Imaging device 202 may be manually handled and controlled (e.g., by a surgeon performing a surgical procedure on a patient). Alternatively, camera head 208 may be coupled to a manipulator arm (e.g., one of manipulator arms 112) of a computer-assisted surgical system (e.g., surgical system 100) and imaging device 202 may be controlled using robotic and/or teleoperation technology.

The distal end of shaft 210 may be positioned at or near a scene that is to be imaged by imaging device 202. For example, the distal end of shaft 210 may be inserted into a patient. In this configuration, imaging device 202 may be used to capture images of anatomy and/or other objects within the scene.

Image sensors 212 may each be implemented by any suitable image sensor, such as a charge coupled device ("CCD") image sensor, a complementary metal-oxide semiconductor ("CMOS") image sensor, or the like. As shown in FIG. 2, image sensors 212 are positioned (e.g., on a PCB) at the distal end of shaft 210. Alternatively, image sensors 212 may be positioned closer to a proximal end of shaft 210, on a PCB inside camera head 208, or outside imaging device 202 (e.g., inside controller 204). In these alternative configurations, optics (e.g., lenses, optical fibers, etc.) included in shaft 210 and/or camera head 208 may convey light from a scene to image sensors 212.

Image sensors 212 are configured to detect (e.g., capture, collect, sense, or otherwise acquire) light. For example, image sensor 212-R is configured to detect the light from a right-side perspective, and image sensor 212-L is configured to detect the light from a left-side perspective. The light detected by image sensors 212 may include, for example, visible light reflected by an object included within the scene and/or fluorescence illumination emitted by a fluorescence imaging agent (e.g., a fluorescent dye, a fluorophore, or a fluorescent protein that has been injected or absorbed into a bloodstream of a patient) within the scene. As will be illustrated below, image sensors 212 may convert the detected light into data representative of one or more images.

First illumination channel 214-1 may be implemented by one or more optical components (e.g., optical fibers, light guides, lenses, etc.). As will be described below, illumination may be provided to the scene by way of first illumination channel 214-1 in imaging device 202 to illuminate a scene.

Controller 204 may be implemented by any suitable combination of hardware and software configured to control and/or interface with imaging device 202. For example, controller 204 may be at least partially implemented by a computing device included in auxiliary system 106. Controller 204 includes a camera control unit ("CCU") 216, an illumination source 218, and a power source 220. Controller 204 may include additional or alternative components as may serve a particular implementation. In some examples, CCU 216 and/or illumination source 218 are alternatively included in imaging device 202 (e.g., on a PCB in camera head 208).

CCU 216 is configured to control various parameters (e.g., activation times, auto exposure, etc.) of image sensors 212. To this end, CCU 216 may be configured to receive and/or generate control signals and transmit the control signals to imaging device 202 (e.g., image sensors 212). As will be described below, CCU 216 may be further configured to receive and process image data from image sensors 212. While CCU 216 is shown in FIG. 2 to be a single unit, CCU 216 may alternatively be implemented by a first CCU configured to control image sensor 212-R and a second CCU configured to control image sensor 212-L.

Illumination source 218 may be configured to generate and emit illumination 222. Illumination 222 (which is also referred herein to as light) may travel by way of a second illumination channel 214-2 included in controller 204 and a third illumination channel 214-3 included in cable 206. At imaging device 202, illumination 222 travels by way of first illumination channel 214-1 to a distal end of shaft 210, where illumination 222 exits to illuminate a scene. Together, first illumination channel 214-1, second illumination channel 214-2, and third illumination channel 214-3 may be referred to herein as illumination channel 214. While illumination source 218 is shown to be a single device in controller 204, illumination source 218 may alternatively include multiple illumination sources each configured to generate and emit differently configured illumination. Additionally, while illumination channel 214 is shown to be a single channel, illumination channel 214 may include multiple different optics (e.g., lenses, optical fibers, waveguides, etc.).

Power source 220 may include circuitry configured to provide electrical power to components included in imaging device 202. Electrical power may be transmitted to imaging device 202 (e.g., to a PCB included in camera head 208) by way of power wiring 224 included in cable 206.

To capture one or more images of a scene, controller 204 (or any other suitable computing device) may activate illumination source 218 and image sensors 212. While activated, illumination source 218 emits illumination 222, which travels via illumination channel 214 to the scene. Image sensors 212 detect illumination reflected from one or more surfaces in the scene. Image sensors 212 (and/or other circuitry included in imaging device 202) may convert the detected light into image data 226 representative of one or more images of the scene. For example, image sensor 212-R outputs image data 226-R representative of images captured from a right-side perspective and image sensor 212-L outputs image data 226-L representative of images captured from a left-side perspective. Image data 226 may have any suitable format.

Image data 226 is transmitted from image sensors 212 to CCU 216. Image data 226 may be transmitted by way of any suitable communication link between image sensors 212 and CCU 216. For example, image data 226 may be transmitted to CCU 216 by way of one or more wires included in cable 206. Additionally or alternatively, image data 226 may be transmitted to CCU 216 by way of one or more optical fibers.

CCU 216 may process (e.g., packetize and/or format) image data 226 and output processed image data 228 (e.g., processed image data 228-R corresponding to image data 226-R and processed image data 228-L corresponding to image data 226-L). Processed image data 228 may be transmitted to an image processor (not shown) for further processing. The image processor may be implemented by one or more computing devices external to imaging system 200, such as one or more computing devices included in surgical system 100 (e.g., in one or more computing devices included within auxiliary system 106). In some examples, the image processor is implemented by a processing facility of surgical system 100. Alternatively, the image processor may be included in controller 204. The image processor may prepare processed image data 228 for display, in the form of one or more still images and/or video content, on one or more display devices (e.g., a stereo viewer of user control system 104 or display monitor 114 of auxiliary system 106).

As mentioned, cable 206 may include one or more communication channels (e.g., wires and/or optical fibers) for transmitting data (e.g., image data 226 and/or control signals) between imaging device 202 and controller 204, a power transmission channel (e.g., one or more power wires) for transmitting electrical power from power source 220 to imaging device 202, and an illumination channel for conveying illumination 222 from illumination source 218 to imaging device 202. Cable 206 may be removably connected to controller 204, thereby enabling cable 206 to be removed from controller 204, such as for cleaning and sterilizing imaging device 202 and cable 206 after usage in a surgical procedure.

The electronic assemblies described herein may be implemented within any of the surgical instruments described herein. For example, as will be described in more detail below, the electronic assemblies described herein may be implemented within an imaging device (e.g., imaging device 202) to provide a moisture barrier for electrical components and/or circuitry disposed within a camera head (e.g., camera head 208) of the imaging device.

Figure 3:
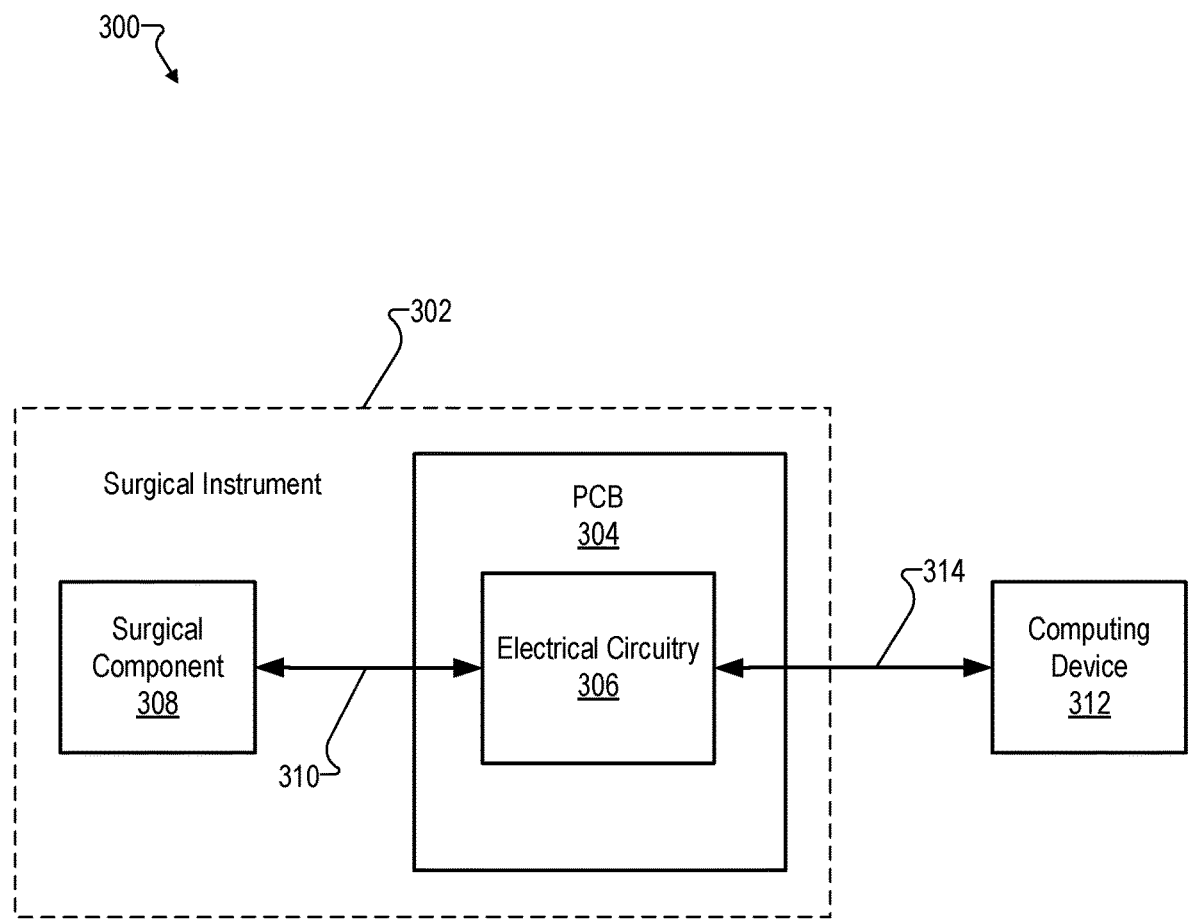
FIG. 3 illustrates an exemplary configuration of an electronic assembly included in a surgical instrument according to principles described herein.

FIG. 3 illustrates an exemplary configuration 300 in which an electronic assembly may be implemented in a surgical instrument 302. As shown, surgical instrument 302 includes a PCB 304, electrical circuitry 306 attached to a surface of PCB 304, and a surgical component 308. Electrical circuitry 306 may be communicatively (e.g., electrically, optically, etc.) connected to surgical component 308 by way of a connection 310. Electrical circuitry 306 may also be communicatively (e.g., electrically, optically, etc.) connected to a computing device 312 located off PCB 304 by way of a connection 314. Each of these components will now be described.

PCB 304 may be configured to mechanically support and electrically couple various electrical components included in electrical circuitry 306. For example, PCB 304 may include conductive pads to which electrical components may be soldered or otherwise electrically coupled, and conductive paths (e.g., traces, vias, etc.) that electrically interconnect the various electrical components.

Electrical circuitry 306 may include any number of passive or active electrical components (e.g., resistors, capacitors, integrated circuits ("ICs"), coils, processors, etc.) interconnected in any suitable manner so as to perform one or more desired circuit operations. For example, electrical circuitry 306 may be configured to receive signals from surgical component 308 by way of connection 310 and/or generate data based on the signals. Electrical circuitry 306 may further be configured to process the data and/or transmit the data to computing device 312 by way of connection 314. In some examples electrical circuitry 306 may implement imaging sensors (e.g., image sensors 212), camera control units (e.g., CCU 216), and/or any other components of an imaging system.

PCB 304 may be disposed within any suitable housing. For example, PCB 304 may be disposed within a camera head (e.g., camera head 208) of an imaging device. PCB 304 may alternatively be disposed within any other type of surgical instrument and/or component as may serve a particular implementation. Additionally, although PCB 304 is shown as being separate from surgical component 308, PCB 304 may also be included in surgical component 308. For example, PCB 304 may be positioned at a distal end of a shaft (e.g., shaft 210) of an imaging device (e.g., imaging device 202) to support one or more imaging sensors (e.g., imaging sensors 212).

Surgical component 308 may include any component configured to be positioned within a surgical area associated with a patient. In some examples, surgical component 308 may be a particular component of a surgical instrument used during a surgical procedure. For example, surgical component 308 may be implemented by a shaft (e.g., shaft 210) of an imaging device (e.g., imaging device 202).

Surgical component 308 may be connected to electrical circuitry 306 by way of connection 310 in any suitable manner. For example, one or more components disposed within surgical component 308 may be electrically, optically, wirelessly, or otherwise coupled to electrical circuitry 306. In this manner, electrical circuitry 306 may receive signals from surgical component 308. For example, surgical component 308 may transmit to electrical circuitry 306 data representative of one or more images captured by imaging sensors included surgical component 308. Additionally or alternatively, surgical component 308 may be configured to receive signals (e.g., control signals) from electrical circuitry 306, such as to control operation of surgical component 308.

Computing device 312 may include any suitable computing device located off PCB 304. For example, computing device 312 may be included in manipulating system 102, user control system 104, or auxiliary system 106. Additionally or alternatively, computing device 312 may be included in any other system (e.g., a display system) as may serve a particular implementation. Computing device 312 may be configured to receive and process data transmitted from electrical circuitry 306. For example, computing device 312 may display one or more images represented by the data on one or more display screens. Additionally or alternatively, computing device 312 may be configured to transmit signals (e.g., control signals) to electrical circuitry 306, such as to control operation of surgical component 308.

Computing device 312 may be connected to electrical circuitry 306 by way of connection 314 in any suitable manner. For example, one or more components disposed within computing device 312 may be electrically, optically, wirelessly, or otherwise coupled to electrical circuitry 306. In this manner, electrical circuitry 306 may transmit signals to and/or receive signals from surgical component 308. In some examples connection 314 is implemented by connection 116-1.

In some examples connection 314 may be broken (e.g., an electrical cable is removed from computing device 312) such that surgical instrument 302 may be processed and sterilized before usage in a surgical procedure. To protect PCB 304 and/or electrical circuitry 306 from moisture that may be present during a surgical procedure and/or a sterilization process, a conformal barrier may be disposed on at least a portion of PCB 304 and/or on electrical circuitry 306. Exemplary electronic assemblies including conformal barriers will now be described.

Figure 4:
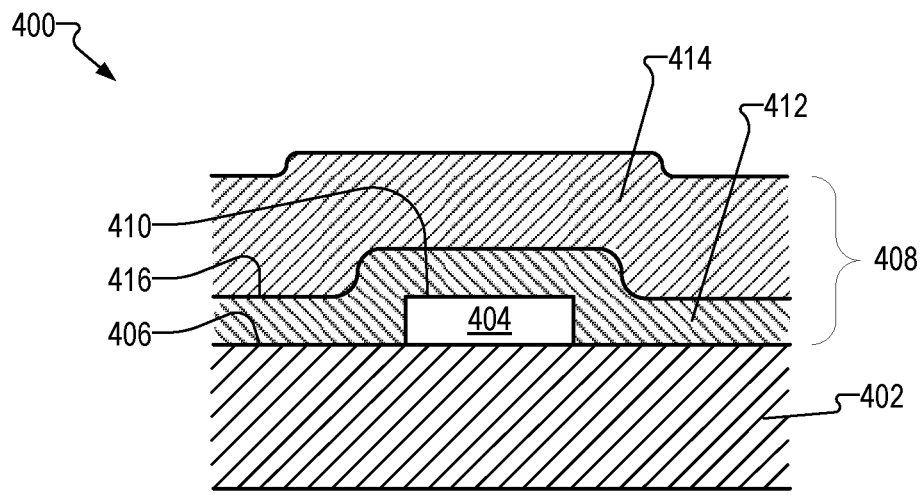
FIG. 4 illustrates a cross-sectional side view of an exemplary electronic assembly according to principles described herein.

FIG. 4 illustrates a cross-sectional side view of an exemplary electronic assembly 400. As shown, electronic assembly 400 includes a PCB 402, an electrical component 404 attached to an upper surface 406 of PCB 402, and a conformal barrier 408 disposed on at least a portion of surface 406 of PCB 402 and on an outer surface 410 of electrical component 404. In some examples PCB 402 is implemented by PCB 304.

Electrical component 404 may implement electrical circuitry 306 and may include one or more passive and/or active electrical components (e.g., resistors, capacitors, ICs, coils, processors, etc.). Outer surface 410 of electrical component 404 includes the surfaces of electrical component 404 that are not attached to or otherwise in direct contact with surface 406 of PCB 402. Accordingly, as shown in FIG. 4 outer surface 410 of electrical component 404 includes an upper surface (e.g., a surface that is parallel to surface 406 of PCB 402) and side surfaces (e.g., surfaces that are perpendicular to surface 406 of PCB 402). Electrical component 404 may be attached to surface 406 of PCB 402 in any suitable manner, such as by mechanical fasteners, soldering, adhesive, etc.

Conformal barrier 408 is disposed on at least a portion of surface 406 of PCB 402 and on outer surface 410 of electrical component 404 such that conformal barrier 408 covers outer surface 410 of electrical component 404 and hermetically seals electrical component 404 between conformal barrier 408 and PCB 402.

As shown in FIG. 4, conformal barrier 408 includes a first barrier layer 412 and a second barrier layer 414. First barrier layer 412 comprises an ALD film, which is formed of any suitable material formed by atomic layer deposition. Suitable materials of the ALD film may include materials that are electrically non-conductive, physically hard, stable at chemical cleaning and sterilization autoclave temperatures (e.g., in some examples up to at least about 121° C., in other examples up to at least about 135° C., and in other examples up to about 150° C.), chemically inert, and/or resistant to oxidation and hydrolysis. In some examples the ALD film is formed of a material comprising one or more oxides, nitrides, carbides, and/or borides of a transition metal, aluminum (Al), cerium (Ce), silicon (Si), or boron (B), or composites (e.g., alloys) thereof (e.g., hafnium silicate (HfSiO$_4$), zirconium silicate (ZrSiO$_4$), etc.). Suitable transition metals may include, without limitation, hafnium (Hf), molybdenum (Mo), palladium (Pd), platinum (Pt), ruthenium (Ru), tantalum (Ta), titanium (Ti), tungsten (W), yttrium (Y), and zirconium (Zr). Exemplary materials may include, without limitation, titanium oxide (TiO$_2$), aluminum oxide (Al$_2$O$_3$), zirconium oxide (ZrO$_2$), cerium oxide (CeO$_2$), hafnium oxide (HfO$_2$), titanium carbide (TiC), zirconium carbide (ZrC), hafnium carbide (HfC), titanium nitride (TiN), tantalum nitride (TaN), tungsten nitride (WN), aluminum nitride (AlN), zirconium nitride (ZrN), hafnium nitride (HfN), hafnium silicate (HfSiO$_4$), and zirconium silicate (ZrSiO$_4$).

Figure 5A:
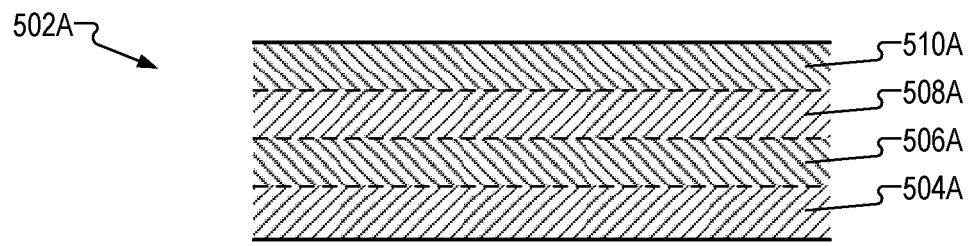
FIGS. 5A and 5B illustrate cross-sectional side views of exemplary ALD films according to principles described herein.
Figure 5B:
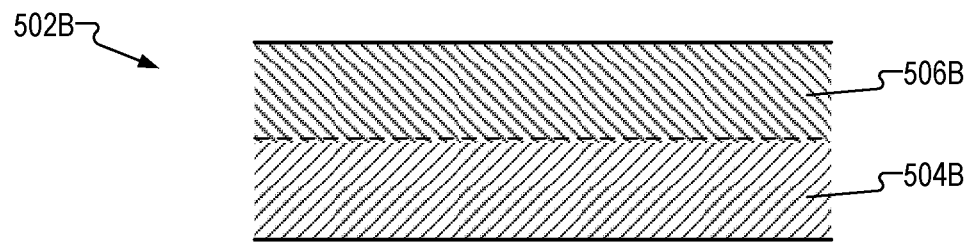

In some examples the ALD film is a single material layer (e.g., ZrO$_2$). In alternative examples the ALD film is a lamination of multiple layers of different materials. FIG. 5A illustrates a cross-sectional side view of an exemplary ALD film 502A formed of a lamination of multiple layers of different materials. As shown, ALD film 502A includes a first layer 504A formed of a first material (e.g., SiO$_2$), a second layer 506A formed of a second material (e.g. Al$_2$O$_3$) different than the first material, a third layer 508A formed of the first material (SiO$_2$), and a fourth layer 510A formed of the second material (Al$_2$O$_3$). Although FIG. 5A shows that ALD 502A includes only two different materials, it will be appreciated that ALD film 502A may include any number of different materials as may suit a particular implementation. Moreover, although FIG. 5A shows four laminated layers of approximately equal thickness, ALD film 502A may include any number of laminated layers of any thickness as may suit a particular implementation. For example, FIG. 5B illustrates a cross-sectional side view of another exemplary ALD film 502B formed of a lamination of two layers of different materials. As shown, ALD film 502B includes a first layer 504B formed of a first material (e.g. ZrO$_2$) and a second layer 506B formed of a second material (e.g., Ti$_2$O) different than the first material.

Referring again to FIG. 4, second barrier layer 414 is disposed on an upper surface 416 of first barrier layer 412. In other words, first barrier layer 412 is disposed between second barrier layer 414 and surface 406 of PCB 402 (e.g., in the regions adjacent to side surfaces of electrical component 404) and between second barrier layer 414 and outer surface 410 of electrical component 404 (e.g., in the region adjacent to the upper surface of electrical component 404).

Second barrier layer 414 is comprised of a material different from first barrier layer 412 (e.g., the material of the ALD film) and is configured to provide conformal barrier protection (e.g., a moisture barrier, scratch resistance, temperature stability, etc.) for PCB 402, electrical component 404, and/or first barrier layer 412. Suitable materials for second barrier layer 414 may include, but are not limited to, Parylene, acrylics, polyurethanes, epoxies, and silicones. In some examples second barrier layer 414 is a single material layer (e.g., Parylene). As used herein Parylene refers to any compound(s) included in the class of chemical vapor deposited poly(p-xylylene) polymers, including but not limited to Parylene C, Parylene AF-4, Parylene SF, Parylene HT, and Parylene N. In alternative examples second barrier layer 414 is a lamination of multiple layers of different materials, similar to ALD film 502 (see FIG. 5).

As shown in FIG. 4, a thickness of second barrier layer 414 is greater than a thickness of first barrier layer 412 because the atomic layer deposition process used to form the ALD film of first barrier layer 412 is slower than processes (e.g., chemical vapor deposition) that may be used to form second barrier layer 414. However, the ALD film is dense, pinhole-free, and provides greater moisture protection than the material of second barrier layer 414 at the same thickness. Accordingly, second barrier layer 414 is thicker than first barrier layer in order to increase the level of moisture and handling protection provided by second barrier layer 414.

In some examples the thickness of first barrier layer 412 ranges from about 2 nanometers (nm) to about 500 nm. In other examples the thickness of first barrier layer 412 ranges from about 2 nm to about 250 nm. In yet other examples the thickness of first barrier layer 412 ranges from about 2 nm to about 100 nm.

In some examples the thickness of second barrier layer is greater than or equal to about 200 nm. In other examples the thickness of second barrier layer 414 ranges from about 200 nm to about 25 microns (25,000 nm). In some examples the thickness of second barrier layer 414 is set based on the desired properties (e.g., temperature stability, moisture blocking, etc.) of second barrier layer 414.

Figure 6:
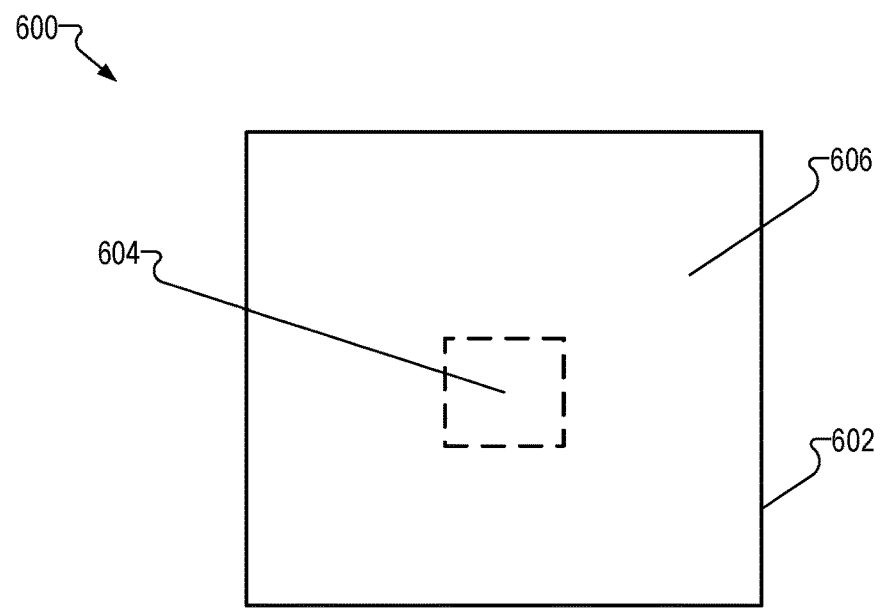
FIGS. 6 and 7 illustrate top views of exemplary configurations of electronic assemblies according to principles described herein.

As mentioned, conformal barrier 408 is disposed on at least a portion of PCB 402. FIG. 6 illustrates a top view of an exemplary configuration 600 of an electronic assembly including a PCB 602, an electrical component 604 attached to a surface of PCB 602, and a conformal barrier 606. As shown, conformal barrier 606 is disposed on (e.g., covers) electrical component 604 and all of the surface of PCB 602 that is not covered by electrical component 604. In this way conformal barrier 606 protects the entire PCB 602, including all conductive pads and conductive paths (e.g., traces, vias, etc.) on or within PCB 602 as well as electrical component 604 attached to PCB 602.

Figure 7:
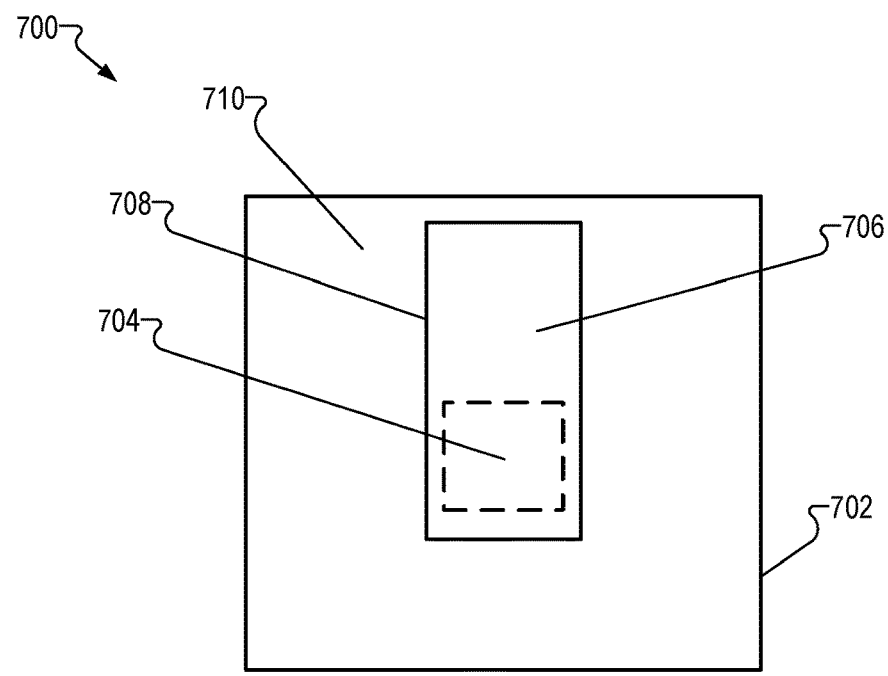

FIG. 7 illustrates a top view of another exemplary configuration 700 of an electronic assembly including a PCB 702, an electrical component 704 attached to a surface of PCB 702, and a conformal barrier 706. As shown, conformal barrier 706 is disposed on (e.g., covers) electrical component 704 but is disposed on only a portion 708 of the surface of PCB 702 that is not covered by electrical component 704. Another portion 710 of the surface of PCB 702 that is not covered by electrical component 704 does not have conformal barrier 706 disposed thereon. This configuration may be used, for example, when all of the conductive pads and conductive paths used in electronic circuitry (e.g., electronic circuitry 304) are included in portion 708 of PCB 702 but not in portion 710 of PCB 702. Limiting the coverage extent of the conformal barrier may reduce processing time.

Referring again to FIG. 4, in some examples the coverage extent of first barrier layer 412 included in conformal barrier 408 may be different from the coverage extent of second barrier layer 414 included in conformal barrier 408. For instance, first barrier layer 412 may be disposed on electrical component 404 and on only a portion of surface 406 of PCB 402 in the manner shown in FIG. 7, while second barrier layer 414 may cover electrical component 404 and all of the surface of PCB 402 that is not covered by electrical component 404 in the manner shown in FIG. 6.

Figure 8:
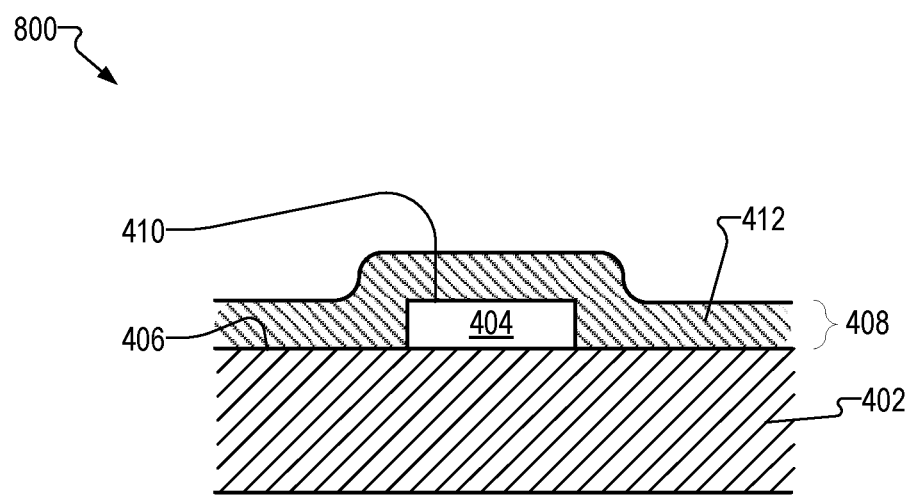
FIGS. 8-10 illustrate cross-sectional side views of exemplary electronic assemblies according to principles described herein.

The foregoing embodiments have described a conformal barrier 408 as including a first barrier layer 412 comprising an ALD film and a second barrier layer 414 comprising a different material, such as Parylene, disposed on the first barrier layer 412. In alternative embodiments conformal barrier 408 may include a single barrier layer comprising an ALD film. FIG. 8 illustrates a cross-sectional side view of an exemplary electronic assembly 800 having a single barrier layer. FIG. 8 is the same as FIG. 4 except that conformal barrier 408 does not include second barrier layer 414 but includes only first barrier layer 412 comprising an ALD film.

Figure 9:
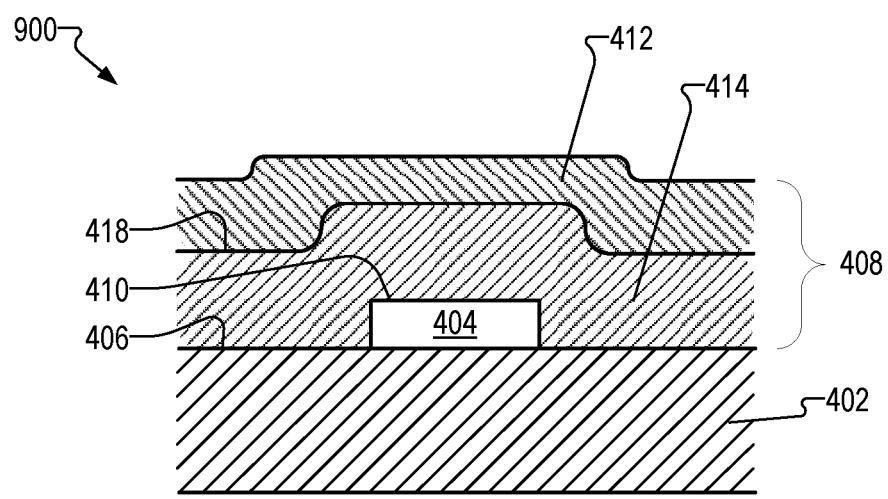

FIG. 9 illustrates a cross-sectional side view of another exemplary electronic assembly 900 in which the order of first barrier layer 412 and second barrier layer 414 is switched. FIG. 9 is the same as FIG. 4 except that second barrier layer 414 is disposed on at least a portion of surface 406 of PCB 402 and on electrical component 404, and first barrier layer 412 comprising an ALD film is disposed on an upper surface 418 of second barrier layer 414.

Figure 10:
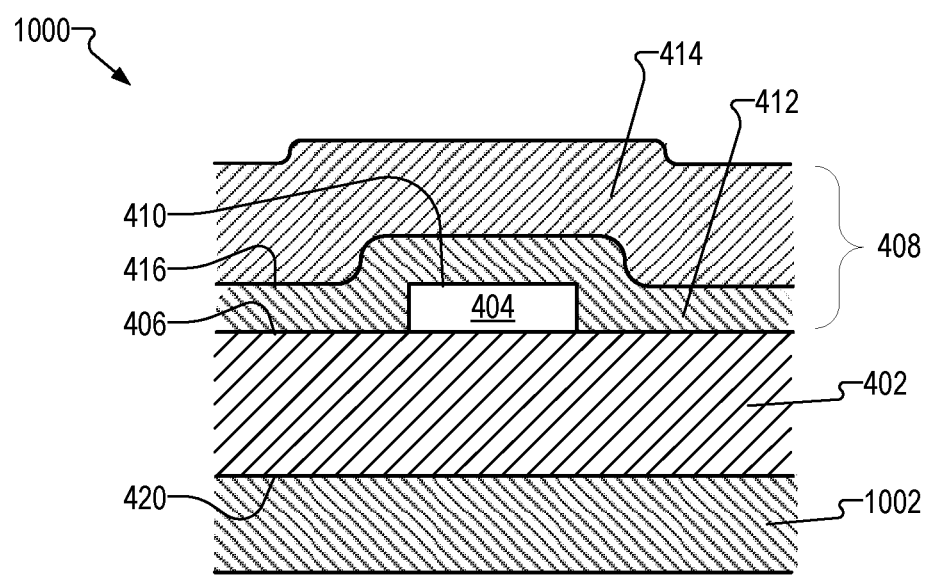

FIG. 10 illustrates a cross-sectional side view of yet another exemplary electronic assembly 1000. FIG. 10 is the same as FIG. 4 except that another conformal barrier 1002 is disposed on at least a portion of a back-side surface 420 of PCB 402. Conformal barrier 1002 may be configured in any of the ways described herein with respect to any of the previously-described conformal barriers.

A method of forming an electronic assembly will now be described with reference to FIGS. 11A to 11D. FIGS. 11A to 11D show cross-sectional side views of an electronic assembly 1100 during different stages of processing. While FIGS. 11A to 11D illustrate an exemplary method according to one embodiment, other embodiments may omit, add to, reorder, combine, and/or modify any of the steps shown in FIGS. 11A to 11D.

Figure 11A:
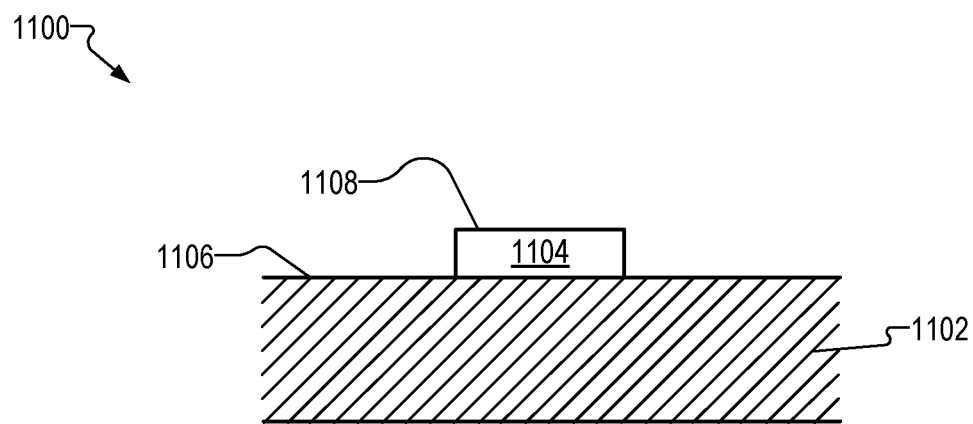
FIGS. 11A-11D illustrate cross-sectional side views of an exemplary electronic assembly during different stages of formation of the electronic assembly according to principles described herein.

As shown in FIG. 11A, processing begins with a PCB 1102 and an electrical component 1104 attached to an upper surface 1106 of PCB 1102. PCB 1102 and electrical component 1104 may be implemented by any of the PCBs and electrical components described herein. In some examples, prior to formation of a first barrier layer the surface 1106 of PCB 1102 and an outer surface 1108 of electrical component 1104 may be pre-cleaned to remove contaminants present on surface 1106 and outer surface 1108. Surface 1106 and outer surface 1108 may be pre-cleaned in any suitable way, such as with a liquid cleaner (e.g., acetate, acetone, a mild acid, etc.).

In alternative examples surface 1106 and outer surface 1108 are pre-cleaned with a plasma surface treatment. In some examples the plasma surface treatment comprises cleaning surface 1106 and outer surface 1008 with an energized gas mixture comprising an inert gas (e.g., argon (Ar), nitrogen gas ($N_2$), etc.) and an oxidizing agent (e.g., oxygen gas ($O_2$)). The plasma ion energies may range from about 10 eV to about 100 eV. The plasma ions of the oxidizing agent are configured to oxidize organic contaminants on surface 1106 and outer surface 1108, thereby increasing the volatility of the organic contaminants to facilitate their ejection from surface 1106 and outer surface 1108. The plasma ions of the inert gas are configured to bombard and aid in the ejection of the surface contaminants. In some examples a concentration of the oxidizing agent in the gas mixture is greater than 0% but less than or equal to about 20% to prevent significant oxidation of exposed metallic surfaces (e.g., soldered contacts, metal contacts, traces, vias, etc.) on PCB 1102 and/or electrical component 1104.

In some examples the plasma surface treatment may be performed in an atomic layer deposition reaction chamber, and/or carried out in accordance with an atomic layer deposition technique. For example, while PCB 1102 is positioned within the reaction chamber the gas mixture may be injected into the reaction chamber in one or more pulses, and the contaminants and gas mixture may be purged from the reaction chamber. In some examples the reaction chamber may be configured with one or more electrodes configured to energize the gas mixture to generate plasma ions. Alternatively, the gas mixture may be energized prior to injection into the reaction chamber. In other examples, the plasma surface treatment can also take place in another chamber separate from the ALD reaction chamber (e.g., a chamber adjacent to the ALD reaction chamber that does not break vacuum).

Figure 11B:
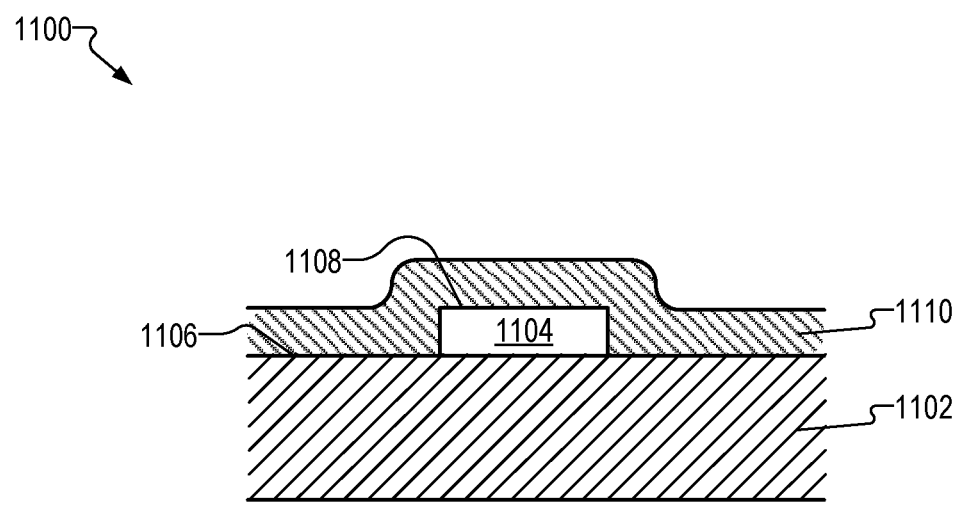

Referring now to FIG. 11B, a first barrier layer 1110 is formed on surface 1106 of PCB 1102 and on outer surface 1108 of electrical component 1104 by atomic layer deposition. First barrier layer 1110 may be formed by any suitable atomic layer deposition technique. For example, while PCB 1102 is positioned within a reaction chamber a first precursor is pulsed into the reaction chamber and then purged, followed by a pulse and purge of a second precursor. This process may be performed and repeated until an ALD film has been grown as desired. First barrier layer 1110 may be configured in any of the ways described herein.

Figure 11C:
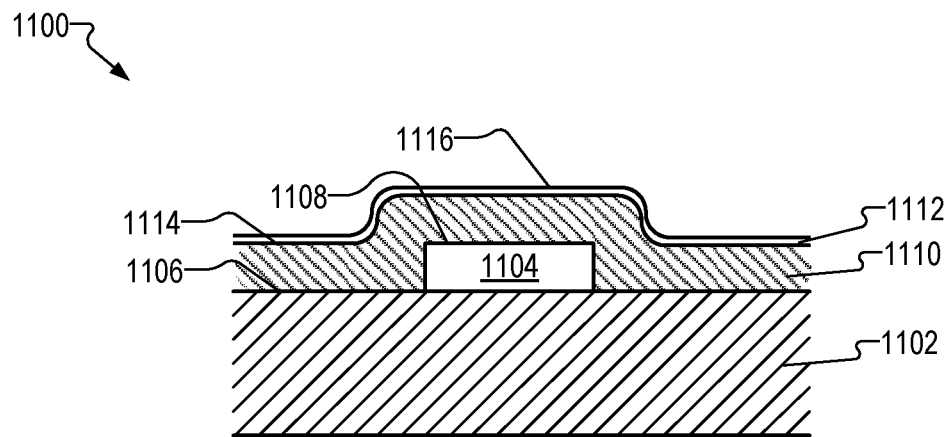

If a second barrier layer is to be formed on first barrier layer 1110, an adhesion promotion layer 1112 may be formed on an upper surface 1114 of first barrier layer 1110, as illustrated in FIG. 11C. Any suitable adhesion promoter material configured to promote adhesion of the second barrier layer to upper surface 1114 of first barrier layer 1110 may be used to form adhesion promotion layer 1112. Suitable materials may include, for example, silane coupling agents such as but not limited to methacryloxypropyl trimethoxysilane (also known and referred to herein as "silane A-174").

Adhesion promotion layer 1112 may be formed on upper surface 1114 of first barrier layer 1110 in any suitable way. In some examples adhesion promotion layer 1112 is formed in accordance with an atomic layer deposition technique. For example, while PCB 1102 is still positioned within the reaction chamber after formation of first barrier layer 1110, water may be injected into the reaction chamber in one or more pulses. The water may react with the ALD film on upper surface 1114 of first barrier layer 1110, thereby forming a layer of reactive hydroxyl groups on upper surface 1114 of first barrier layer 1110. Other reaction byproducts may be purged from the reaction chamber.

An adhesion promoter may be injected (e.g., by one or more pulses) into the reaction chamber, wherein a reactive end of the adhesion promoter reacts with the hydroxyl groups on upper surface 1114 of first barrier layer 1110 to form adhesion promotion layer 1112 bonded to upper surface 1114 of first barrier layer 1110. For example, silane A-174 and water may be injected (either simultaneously or in alternating pulses) into the reaction chamber. The water may hydrolyze the methoxysilane functional groups of silane A-174 to form reactive silanol groups, which may condense with other silanol groups of silane A-174 to form silane A-174 oligomers. The silanol groups of the silane A-174 oligomers may also condense with the hydroxyl groups on upper surface 1114 of first barrier layer 1110. Upper surface 1114 of first barrier layer 1110 may be dried or cured, such as by purging the reaction chamber with an inert gas and/or heating, to promote the formation of covalent bonds between the silane A-174 oligomers and upper surface 1114 of first barrier layer 1110 (i.e., the upper surface of the ALD film of first barrier layer 1110). An upper surface 1116 of adhesion promotion layer 1112 thus comprises reactive methacryloxy groups of the silane A-174 adhesion promoter. As will be explained below, the methacryloxy groups on upper surface 1116 may be used to initiate polymerization of the second barrier layer.

Figure 11D:
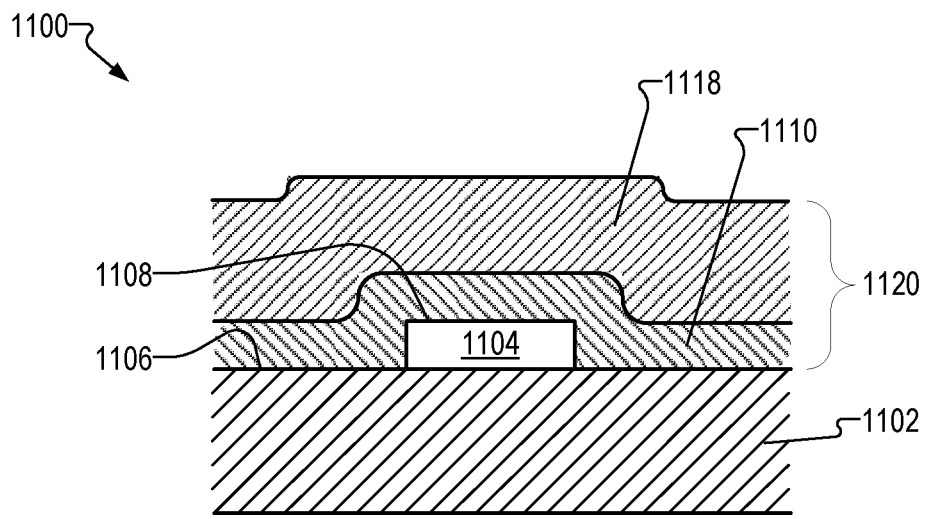

Referring now to FIG. 11D, a second barrier layer 1118 may be formed on first barrier layer 1110. Second barrier layer 1118 may be formed in any suitable way, such as by copolymerization via chemical vapor deposition. For example, second barrier layer 1118 may be formed by copolymerization of monomers of Parylene and the reactive methacryloxy group on upper surface 1116 of adhesion promotion layer 1112 via a free radical addition reaction. The polymerization process may continue until second barrier layer 1118 has a desired thickness. Second barrier layer 1118 may be configured in any of the ways described herein.

As shown in FIG. 11D, the resulting electronic assembly 1100 includes a conformal barrier 1120 disposed on outer surface 1108 of electrical component 1104 and on surface 1106 of PCB. Conformal barrier 1120 includes first barrier layer 1110 and second barrier layer 1118. First barrier layer 1110 comprises an ALD film and second barrier layer 1118 comprises a different conformal barrier material such as Parylene.

It will be recognized that various modifications may be made to this process. In some examples, a mask may be used to produce a conformal barrier that does not cover the entire surface 1106 of PCB that is not covered by electrical component 1104. In other examples, additional conformal barriers may be formed on second barrier layer 1118. Such additional conformal barriers may comprise one or more other ALD films and/or other conformal barrier materials.

Figure 12:
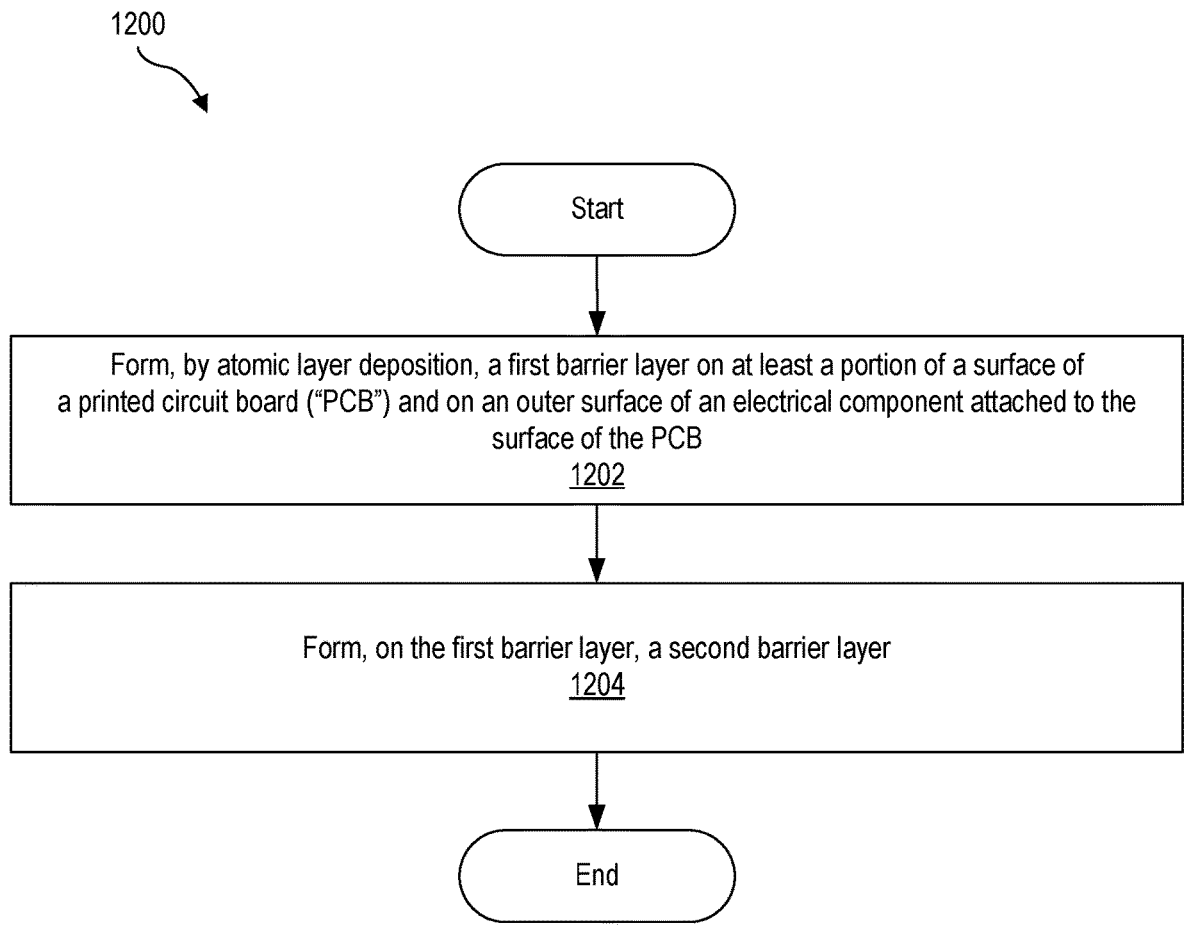
FIGS. 12 and 13 illustrate exemplary methods of forming an electronic assembly according to principles described herein.

FIG. 12 shows an exemplary method 1200 of forming an electronic assembly. While FIG. 12 illustrates exemplary operations according to one embodiment, other embodiments may omit, add to, reorder, combine, and/or modify any of the steps shown in FIG. 12.

In operation 1202, a first barrier layer is formed by atomic layer deposition on at least a portion of a surface of a PCB and on an outer surface of an electrical component attached to the surface of the PCB. Operation 1202 may be performed in any of the ways described herein.

In operation 1204, a second barrier layer is formed on the first barrier layer. Operation 1204 may be performed in any of the ways described herein.

Figure 13:
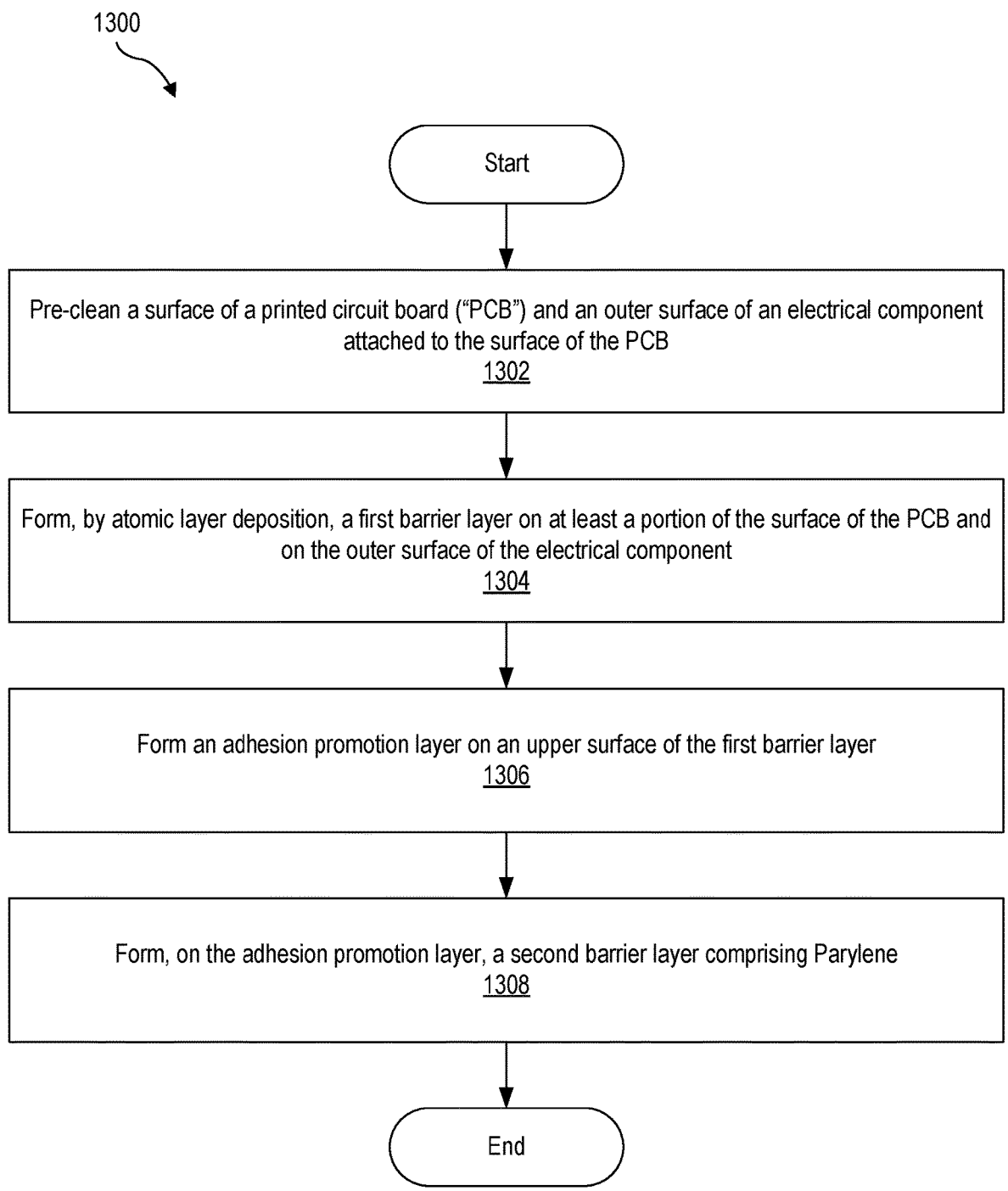

FIG. 13 shows another exemplary method 1300 of forming an electronic assembly. While FIG. 13 illustrates exemplary operations according to one embodiment, other embodiments may omit, add to, reorder, combine, and/or modify any of the steps shown in FIG. 13.

In operation 1302, a surface of a PCB and an outer surface of an electrical component attached to the surface of the PCB are pre-cleaned. Operation 1302 may be performed in any of the ways described herein, such as by a plasma surface treatment.

In operation 1304, a first barrier layer is formed by atomic layer deposition on at least a portion of the surface of the PCB and on the outer surface of the electrical component. Operation 1304 may be performed in any of the ways described herein.

In operation 1306, an adhesion promotion layer is formed on an upper surface of the first barrier layer. Operation 1306 may be performed in any of the ways described herein.

In operation 1308, a second barrier layer comprising Parylene is formed on the first barrier layer. Operation 1308 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
    forming, by atomic layer deposition, a first barrier layer on a surface of a printed circuit board ("PCB") and on an outer surface of an electrical component attached to the surface of the PCB;
    forming an adhesion promotion layer on a surface of the first barrier layer; and
    forming, on the adhesion promotion layer, a second barrier layer comprising Parylene.

2. The method of claim 1, wherein the forming the adhesion promotion layer comprises:
    functionalizing the surface of the first barrier layer with hydroxyl groups; and
    reacting an adhesion promoter with the hydroxyl groups.

3. The method of claim 2, wherein the adhesion promoter comprises a silane coupling agent.

4. The method of claim 2, wherein the functionalizing the surface of the first barrier layer with the hydroxyl groups comprises reacting water with the surface of the first barrier layer.

5. The method of claim 4, wherein:
    the first barrier layer and the adhesion promotion layer are formed within a reaction chamber; and
    the adhesion promoter and the water are injected into the reaction chamber simultaneously or in alternating pulses.

6. The method of claim 1, wherein the adhesion promotion layer comprises methacryloxy groups at a surface of the adhesion promotion layer.

7. The method of claim 6, wherein the second barrier layer is formed by copolymerization of monomers of Parylene and the methacryloxy groups.

8. The method of claim 1, wherein the first barrier layer comprises at least one of an oxide, a nitride, a carbide, or a boride of a transition metal, aluminum, cerium, silicon, or boron.

9. The method of claim 1, wherein the first barrier layer comprises at least one of hafnium oxide, cerium oxide, hafnium silicate, or zirconium silicate.

10. The method of claim 1, further comprising pre-cleaning the surface of the PCB with a plasma surface treatment prior to forming the first barrier layer.

11. The method of claim 10, wherein:
    the plasma surface treatment comprises cleaning the surface of the PCB with a gas mixture comprising argon (Ar) and oxygen ($O_2$); and a concentration of the oxygen in the gas mixture is less than or equal to about 20%.

12. The method of claim 11, wherein ion energies in the plasma surface treatment range from about 10 eV to about 100 eV.

13. An electronic assembly comprising:
a printed circuit board ("PCB");
an electrical component attached to a surface of the PCB; and
a conformal barrier disposed on at least a portion of the surface of the PCB and on an outer surface of the electrical component, the conformal barrier comprising:
 a first barrier layer comprising an atomic layer deposited ("ALD") film; and
 a second barrier layer comprising Parylene and coupled with the first barrier layer by way of an adhesion promotion layer.

14. The electronic assembly of claim 13, wherein the adhesion promotion layer comprises a silane coupling.

15. The electronic assembly of claim 14, wherein the silane coupling comprises a methacryloxy silane.

16. The electronic assembly of claim 15, wherein the methacryloxy silane comprises methacryloxypropyl trimethoxysilane.

17. The electronic assembly of claim 13, wherein the ALD film comprises at least one of an oxide, a nitride, a carbide, or a boride of a transition metal, aluminum, cerium, silicon, or boron.

18. The electronic assembly of claim 13, wherein the ALD film comprises at least one of hafnium oxide, cerium oxide, hafnium silicate, or zirconium silicate.

19. An imaging device comprising:
a camera head comprising:
 a printed circuit board ("PCB");
 electrical circuitry on the PCB and configured to receive and process captured image signals; and
 a conformal barrier disposed on at least a portion of the PCB and on the electrical circuitry, the conformal barrier comprising:
  a first barrier layer comprising an atomic layer deposited ("ALD") film; and
  a second barrier layer comprising Parylene.

20. The imaging device of claim 19, wherein the first barrier layer is coupled with the second barrier layer by way of an adhesion promotion layer.

* * * * *